(12) United States Patent
Okawa et al.

(10) Patent No.: US 6,423,008 B1
(45) Date of Patent: Jul. 23, 2002

(54) ULTRASONIC PROBE

(75) Inventors: Eiichi Okawa, Yokohama; Takashi Suzuki, Tokyo, both of (JP)

(73) Assignee: Matsushita Electric Industrial Co., Ltd., Osaka (JP)

(*) Notice: Subject to any disclaimer, the term of this patent is extended or adjusted under 35 U.S.C. 154(b) by 0 days.

(21) Appl. No.: 09/993,133

(22) Filed: Nov. 14, 2001

(30) Foreign Application Priority Data

Nov. 17, 2000 (JP) ........................................ 2000-350749

(51) Int. Cl.[7] .................................................. A61B 8/00
(52) U.S. Cl. ...................................................... 600/459
(58) Field of Search ............................... 600/459, 443, 600/463, 442, 437; 620/460

(56) References Cited

U.S. PATENT DOCUMENTS 4,869,258 A * 9/1989 Hetz ........................... 600/459
5,771,896 A * 6/1998 Sliwa et al. .................. 600/462
6,036,646 A * 3/2000 Barthe et al. ................ 128/916
6,325,760 B1 * 12/2001 Takanori et al. ............. 600/459

* cited by examiner

*Primary Examiner*—Francis J. Jaworski
*Assistant Examiner*—Maulin Patel
(74) *Attorney, Agent, or Firm*—Pearne & Gordon LLP

(57) ABSTRACT

Herein disclosed is an ultrasonic probe comprising a transducer for transducing an electric signal into and out of an ultrasonic wave, an electromagnet motor for rotating the transducer, a frame structure for rotatably supporting the electromagnet motor, a brake mechanism for allowing the electromagnet motor to be braked. The ultrasonic probe thus constructed can actuate the brake mechanism to brake the electromagnet motor to prevent the transducer from rotating when the electromagnet motor is stopped and release the brake mechanism to enable the transducer to rotate when the electromagnet motor is rotating, thereby protecting the transducer from a large shock caused by the electromagnet motor especially when the ultrasonic probe is dropped.

16 Claims, 10 Drawing Sheets

ULTRASONIC PROBE

BACKGROUND OF THE INVENTION

1. Field of the Invention

The present invention relates to an ultrasonic probe for and a method of acquiring a tomographic image and other graphic images to be taken from the internal organs of a human body by taking advantage of an ultrasound, and more particularly to an ultrasonic probe for and a method of acquiring a tomographic image and other graphic images to be used for the diagnosis by doctors in the hospitals.

2. Description of the Related Art

In recent years, there have been developed and used various kinds of ultrasonic probes which are designed to probe the internal organs of the human body to assist the doctors in diagnosing the human body in the hospitals. Among those ultrasonic probes, there are two types of ultrasonic probes the first one of which is constructed to be moved on while being kept in touch with the human body's skin to probe the solid internal organs such as livers and pancreas from the outside of the human body, and the second one of which is inserted into the hollow internal organs of the human body including stomachs, rectums and vaginas to probe the hollow internal organs of the human body. Both of the forgoing ultrasonic probes are adapted to emit an ultrasonic wave to the targeted portions of the human body before receiving an ultrasonic wave echoed from the targeted portions of the human body. The ultrasonic wave is transformed by the ultrasonic probe in a conventional manner into an electric signal that is processed into a tomographic image to be displayed on a display unit.

The ultrasonic wave probe is provided at its leading end with an ultrasonic wave probe unit comprising a transducer for transducing an electric signal into and out of an ultrasonic wave, and an electromagnet motor for rotating the transducer within a predetermined rotation angle. The ultrasonic wave probe of this type provided with an ultrasonic wave probe unit as constructed in the above is disclosed in a publication such as for example a Japanese laid-open publication No. 70268/2000.

The conventional ultrasonic wave probe of this type, however, encounters such a problem that the transducer may be rotated unrestrictedly while the electromagnet motor is stopped to drive to rotate the transducer, and subject to breakage by a large shock caused by the electromagnet motor especially when the ultrasonic wave probe is dropped resulting from the fact that the transducer is directly mounted on the electromagnet motor.

The present invention is made with a view to overcoming the previously mentioned drawback inherent to the conventional ultrasonic wave probe.

SUMMARY OF THE INVENTION

It is therefore an object of the present invention to provide an ultrasonic probe which can keep the transducer from rotating by braking the electromagnet motor when the electromagnet motor is stopped. This makes it possible to protect the transducer from a large shock caused by the electromagnet motor especially when the ultrasonic wave probe is dropped It is another object of the present invention to provide an ultrasonic probe which can prevent the transducer from rotating by actuating a brake mechanism when the electromagnet motor is stopped. This makes it possible to protect the transducer from a large shock caused by the electromagnet motor especially when the ultrasonic probe is dropped.

According to one aspect of the present invention, there is provided an ultrasonic probe, comprising: a housing; a frame structure accommodated in the housing and held stationary with respect to the housing; an electromagnet motor rotatably supported by the frame structure in the housing; a transducer fixedly supported by the electromagnet motor in the housing to transduce an ultrasonic wave to and from an electric signal; a brake mechanism fixedly supported by the frame structure in the housing and operative to assume a braking state allowing the electromagnet motor to be braked and a brake-releasing state allowing the electromagnet motor to be released from being braked. The above electromagnet motor is released from being braked by the brake mechanism when the electromagnet motor is driven to rotate while the electromagnet motor is braked by the brake mechanism when the electromagnet motor is stopped.

It is desirable that the above frame structure includes a bottom wall portion and a side wall portion integrally formed with the bottom wall portion to form a hollow chamber, and a window cover securely mounted on the side wall portion of the frame structure to form a closed chamber having the electromagnet motor received therein. The above window cover may be made of an ultrasonic wave transmission material to have the transducer transduce the ultrasonic wave to and from the electric signal.

The above window cover and the frame structure are desirably combined to define a hermetically sealed chamber filing therein a coupling liquid to assist the transducer in transducing the ultrasonic wave to and from the electric signal.

Preferably, the transducer includes a main body having a top surface, and a plurality of piezoelectric elements arranged on the top surface of the main body in spaced relationship with each other along the center axis of the electromagnet motor.

The piezoelectric elements may be in the form of a rectangular shape having a short edge extending along the center axis of the electromagnet motor.

It is desirable that the above window cover has inner and outer surfaces arcuately formed and the main body of the transducer has an outer surface arcuately formed in parallel and spaced relationship with the inner surface of the window cover.

The electromagnet motor preferably includes a rotor portion having a center axis and a pair of side surfaces, and a pair of shaft portions each having a center axis. The shaft portions may be respectively secured to the side surfaces with the center axes being respectively in alignment with the center axis of the rotor portion and rotatably supported by the frame structure.

It is desirable that the frame structure includes a base plate portion, and a pair of stand portions spaced apart from each other along with the rotation axis of the electromagnet motor. The electromagnet motor may include a rotor portion having a center axis and a pair of side surfaces, and a pair of shaft portions each having a center axis. The shaft portions may be respectively secured to the side surfaces with the center axes being respectively in alignment with the center axis of the rotor portion and rotatably supported by the frame structure. The shaft portions may be respectively rotatably supported by the stand portions of the frame structure.

The ultrasonic probe thus constructed can prevent the transducer from rotating by braking the electromagnet motor when the electromagnet motor is stopped. This makes it possible to protect the transducer from a large shock caused by the electromagnet motor especially when the ultrasonic wave probe is dropped.

According to the present invention, the electromagnet motor of the ultrasonic probe has a peripheral portion formed with a cavity. It is desirable that the brake mechanism includes a magnetic frame securely mounted on the frame structure and formed with a chamber therein, an electromagnet coil received in the chamber of the magnetic frame and partly secured to the magnetic frame. The electromagnet coil may be in the form of a cylindrical hollow shape. The brake mechanism desirably further include an electromagnet shaft partly received in the chamber of the magnetic frame in axial alignment with the electromagnet coil and supported by the magnetic frame, and a second longitudinal portion projecting inwardly of the electromagnet coil and the magnetic frame.

The electromagnet shaft may have a first longitudinal portion projecting outwardly of the magnetic frame. The electromagnet shaft may be axially movable with respect to the magnetic frame and the electromagnet coil to assume two operation states consisting of a first operation state under which the electromagnet shaft is projected to an extremely projected position with respect to the electromagnet coil and a second operation state under which the electromagnet shaft is retracted to an extremely retracted position with respect to the electromagnet coil. The brake mechanism desirably further include electromagnet shaft urging means for resiliently urging the electromagnet shaft toward the first operation state under which the first longitudinal portion of the electromagnet shaft is partly brought into engagement with the cavity of the electromagnet motor.

The ultrasonic probe thus constructed can hold the transducer from rotating by braking the electromagnet motor when the electromagnet motor is stopped. This makes it possible to protect the transducer from a large shock caused by the electromagnet motor especially when the ultrasonic wave probe is dropped.

According to the present invention, the above first longitudinal portion of the electromagnet shaft is integrally formed with a first flange portion, and the second longitudinal portion of the electromagnet shaft is integrally formed with a second flange portion, and in which the electromagnet shaft urging means is constituted by a helical coil spring disposed to surround the first longitudinal portion of the electromagnet shaft and to have one end engaged with the first flange portion and the other end engaged with the electromagnet frame.

The above electromagnet motor may be operative to assume a stop position under which the electromagnet motor is stopped with respect to the frame structure with the cavity being in opposing relationship with the first longitudinal portion of the electromagnet shaft. The ultrasonic probe according to the present invention may further comprise electromagnet motor urging means for resiliently urging the electromagnet motor toward the stop position of the electromagnet motor.

The above electromagnet motor may be operative to assume a stop position under which the electromagnet motor is stopped with respect to the frame structure with the cavity being in opposing relationship with the first longitudinal portion of the electromagnet shaft. According to the present invention, the ultrasonic probe may further comprise electromagnet motor urging means for resiliently urging the electromagnet motor in the rotation direction of the electromagnet motor toward the stop position of the electromagnet motor, and electromagnet motor stopping means for stopping the electromagnet motor from being rotated over the stop position.

It is desirable that the electromagnet motor urging means is constituted by a helical coil spring having one end secured to the electromagnet motor and the other end secured to the frame structure, and the electromagnet motor stopping means is constituted by a projected pin projecting axially outwardly of the side surface of the electromagnet motor. The projected pin preferably has a rotation path on which the projected pin is rotatable together with the electromagnet motor, and a stop member securely formed on the frame structure to project to the rotation path of the projected pin to ensure that the electromagnet motor is resiliently urged by the helical coil spring and stopped by the projected pin and the stop member under the stop state under which the cavity is in opposing relationship with the first longitudinal portion of the electromagnet shaft.

In the ultrasonic probe according to the present invention, the electromagnet motor is resiliently urged toward the stop position by the electromagnet motor urging means and stopped with respect to the frame structure with the cavity being opposing relationship with the first longitudinal portion of the electromagnet shaft regardless of the current rotation angle of the electromagnet motor to ensure to prevent the electromagnet motor from rotating.

The aforesaid brake mechanism includes a gear member having a center axis and securely mounted on the side surface of the electromagnet motor with the center axis being aligned with the center axis of the electromagnet motor, the gear member having a plurality of teeth equally spaced apart from one another in the circumferential direction of the gear member, and a plurality of recesses each arranged and disposed between the adjacent two teeth, a magnetic frame securely mounted on the frame structure and formed with a chamber therein, an electromagnet coil received in the chamber of the magnetic frame and partly secured to the magnetic frame, the electromagnet coil being in the form of a cylindrical hollow shape, an electromagnet shaft partly received in the chamber of the magnetic frame in axial alignment with the electromagnet coil and supported by the magnetic frame and in opposing relationship with the gear member, the electromagnet shaft having a first longitudinal portion projecting outwardly of the magnetic frame and a second longitudinal portion projecting inwardly of the electromagnet coil and the magnetic frame, the electromagnet shaft being axially movable with respect to the magnetic frame and the electromagnet coil to assume two operation states consisting of a first operation state under which the electromagnet shaft is projected to an extremely projected position with respect to the electromagnet coil and a second operation state under which the electromagnet shaft is retracted to an extremely retracted position with respect to the electromagnet coil, the first longitudinal portion of the electromagnet shaft having a leading end portion in the form of a pawl shape, electromagnet shaft urging means for resiliently urging the electromagnet shaft toward the first operation state under which the leading portion of the first longitudinal portion of the electromagnet shaft is partly brought into meshing engagement with one of the recesses of the gear member.

In the ultrasonic probe of the third embodiment according to the present invention, the leading portion of the electromagnet shaft is movable to be brought into and out of meshing engagement with one of the recesses of the gear member regardless of the current rotation angle of the electromagnet motor to ensure to prevent the electromagnet motor from rotating.

The aforesaid electromagnet motor may include a rotor portion having a center axis and a pair of side surfaces, and a pair of shaft portions each having a center axis, the shaft portions being respectively secured to the side surfaces with the center axes being respectively in alignment with the center axis of the rotor portion and rotatably supported by the frame structure.

The aforesaid brake mechanism may include a first electromagnet member securely mounted on the peripheral wall of the rotor portion of the electromagnet motor, a magnetic frame securely mounted on the frame structure and formed with a chamber therein, an electromagnet coil received in the chamber of the magnetic frame and partly secured to the magnetic frame, the electromagnet coil being in the form of a cylindrical hollow shape, a second electromagnet member partly received in the chamber of the magnetic frame in axial alignment with the electromagnet coil and supported by the magnetic frame to be directed toward the first electromagnet member to ensure that the first and second electromagnet members repel each other when the electromagnet coil is energized.

The aforesaid magnetic frame preferably includes a bottom wall portion securely mounted on the frame structure, and a side wall portion integrally formed with the bottom wall portion, whereby the bottom wall portion and the side wall portion of the magnetic frame and the first electromagnet member collectively define a chamber to receive the electromagnet coil, the bottom wall portion and the side wall portion of the magnetic frame and the first electromagnet member is made of a magnetic substance.

In the ultrasonic probe thus constructed, the rotor portion is stopped from rotating regardless of the current rotation angle of the electromagnet motor to ensure to prevent the transducer from rotating. Furthermore, the brake mechanism can be constructed without mechanical moving parts, thereby improving the performance and reliability of the ultrasonic probe.

BRIEF DESCRIPTION OF THE DRAWINGS

The features and advantages of the ultrasonic probe according to the present invention will more clearly be understood from the following description taken in conjunction with the accompanying drawings in which.

DESCRIPTION OF THE PREFERRED EMBODIMENTS

Figure 1:
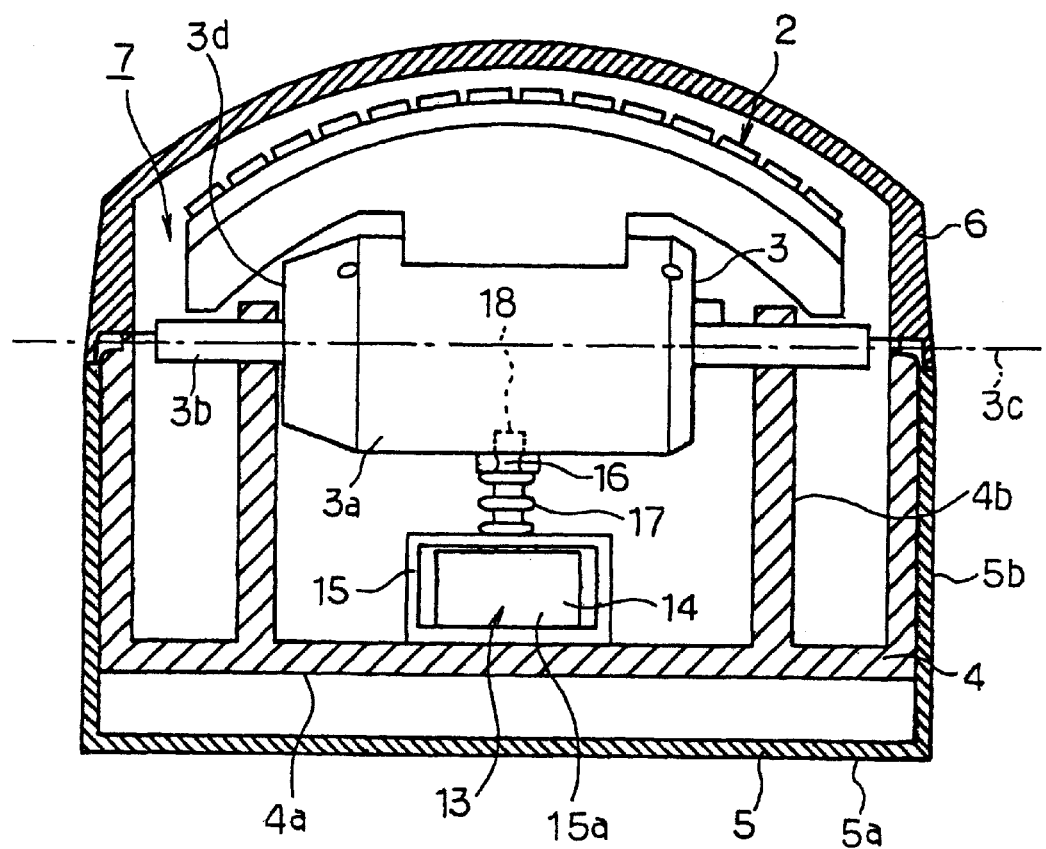
FIG. 1 is a cross-sectional view of a first embodiment of the ultrasonic probe according to the present invention.

The embodiments according to the present invention will be described with reference to the drawings hereinafter.

Referring to FIGS. 1 to 4 of the drawings, there is shown a first preferred embodiment of the ultrasonic probe embodying the present invention. The ultrasonic probe thus shown in FIG. 1 comprises a housing 5, an electromagnet motor 3, a frame structure 4, a transducer 2, and a brake mechanism 13.

The frame structure 4 is accommodated in the housing 5 and held stationary with respect to the housing 5. The electromagnet motor 3 is rotatably supported by the frame structure 4 in the housing 5. The transducer 2 is fixedly supported by the electromagnet motor 3 in the housing 5 to transduce an ultrasonic wave to and from an electric signal. The brake mechanism 13 is fixedly supported by the frame structure 4 in the housing 5 and operative to assume a braking state allowing the electromagnet motor 3 to be braked and a brake-releasing state allowing the electromagnet motor 3 to be released from being braked.

This means that the electromagnet motor 3 is released from being braked by the brake mechanism 13 when the electromagnet motor 3 is driven to rotate while the electromagnet motor 3 is braked by the brake mechanism 13 when the electromagnet motor 3 is stopped.

The housing 5 includes a bottom wall portion 5a and a side wall portion 5b integrally formed with the bottom wall portion 5a to form a hollow chamber. The housing 5 further includes a window cover 6 securely mounted on the side wall portion 5b of the housing 5 to form a closed chamber having the electromagnet motor 3 received therein. The window cover 6 is made of an ultrasonic wave transmission material to have the transducer 2 transduce the ultrasonic wave to and from the electric signal.

The window cover 6 and the frame structure 4 are combined to define a hermetically sealed chamber filling therein a coupling liquid 7 to assist the transducer 2 in transducing the ultrasonic wave to and from the electric signal.

Figure 2:
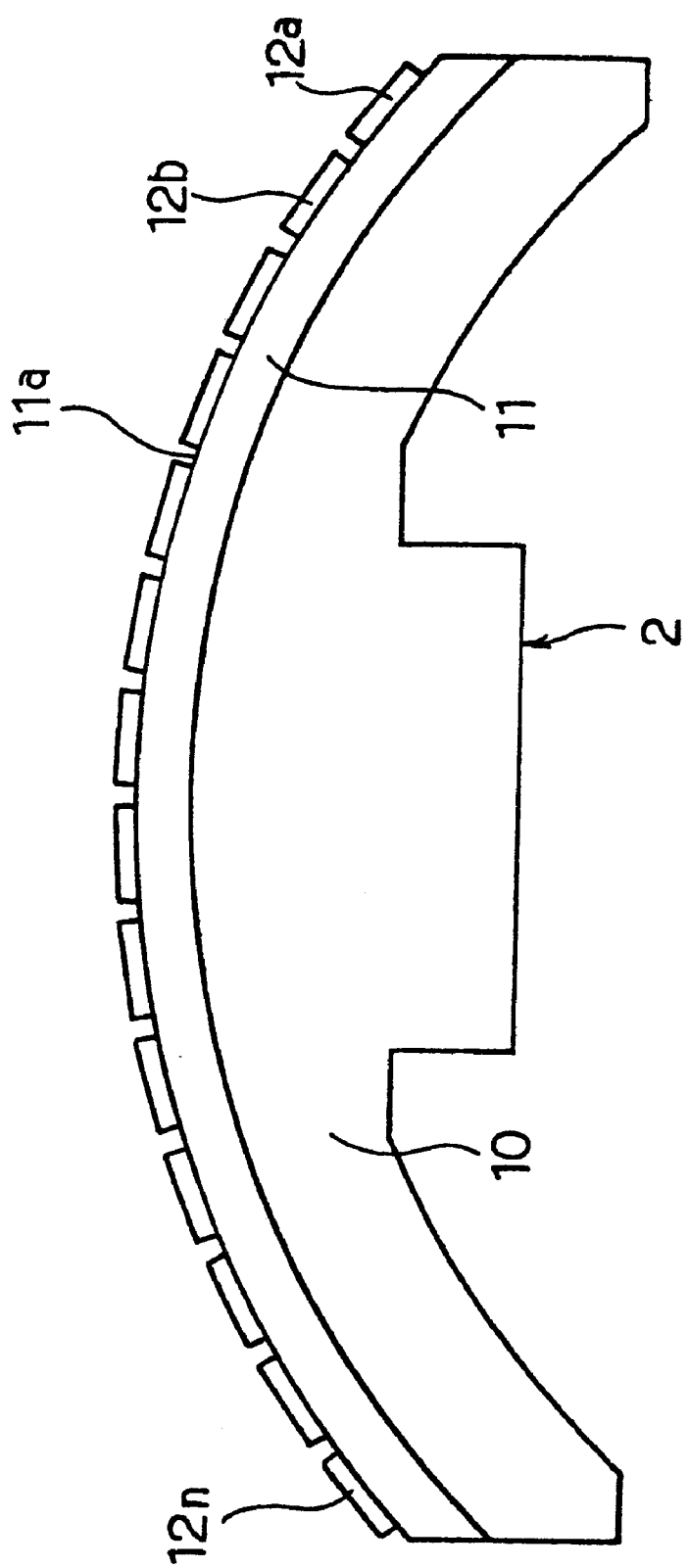
FIG. 2 is a cross-sectional view of a transducer forming part of the ultrasonic probe shown in FIG. 1.

As will be best shown in FIG. 2, the transducer 2 includes a main body 10, 11 having a top surface 11a, and a plurality of piezoelectric elements 12a to 12n arranged on the top surface 11a of the main body 10, 11 in spaced relationship with one another along the center axis 3c of the electromagnet motor 3. The main body 10, 11 is composed of a frame portion 10 and a supporting portion 11.

The piezoelectric elements 12a to 12n are arranged on the main body 10, 11 of the transducer 2 in spaced relationship with one another along the center axis 3c of the electromagnet motor 3. Each of the piezoelectric elements 12a to 12n is in the form of a rectangular shape having a short side extending along the center axis 3c of the electromagnet motor 3.

Returning to FIG. 1, the window cover 6 has inner and outer surfaces arcuately formed and the main body 10, 11 of the transducer 2 has an outer surface arcuately formed in parallel and spaced relationship with the inner surface of the window cover 6.

The electromagnet motor 3 includes a rotor portion 3a having a center axis 3c and a pair of side surfaces 3d, and a pair of shaft portions 3b each having a center axis. The shaft portions 3b are respectively secured to the side surfaces 3d with the center axes being respectively in alignment with the center axis 3c of the rotor portion 3a and rotatably supported by the frame structure 4.

The frame structure 4 includes a base plate portion 4a, and a pair of stand portions 4b spaced apart from each other along with the rotation axis of the electromagnet motor 3, and in which the electromagnet motor 3 includes a rotor portion 3a having a center axis 3c and a pair of side surfaces 3d, and a pair of shaft portions 3b each having a center axis. The shaft portions 3b are respectively secured to the side surfaces 3d with the center axes being respectively in alignment with the center axis 3c of the rotor portion 3a and rotatably supported by the frame structure 4. The shaft portions 3b are respectively rotatably supported by the stand portions 4b of the frame structure 4. The electromagnet motor 3 has a peripheral portion 3a formed with a cavity 18.

Figure 3:
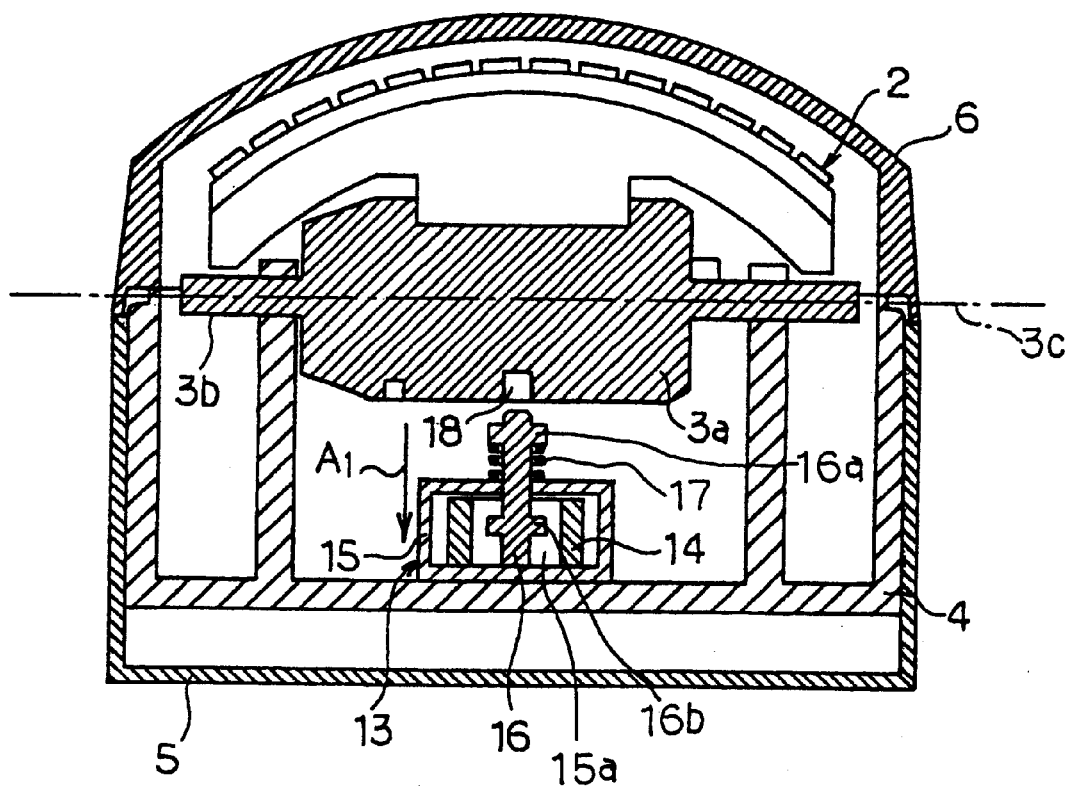
FIG. 3 is a cross-sectional view of the ultrasonic probe shown in FIG.1 when a brake mechanism is released.
Figure 4:
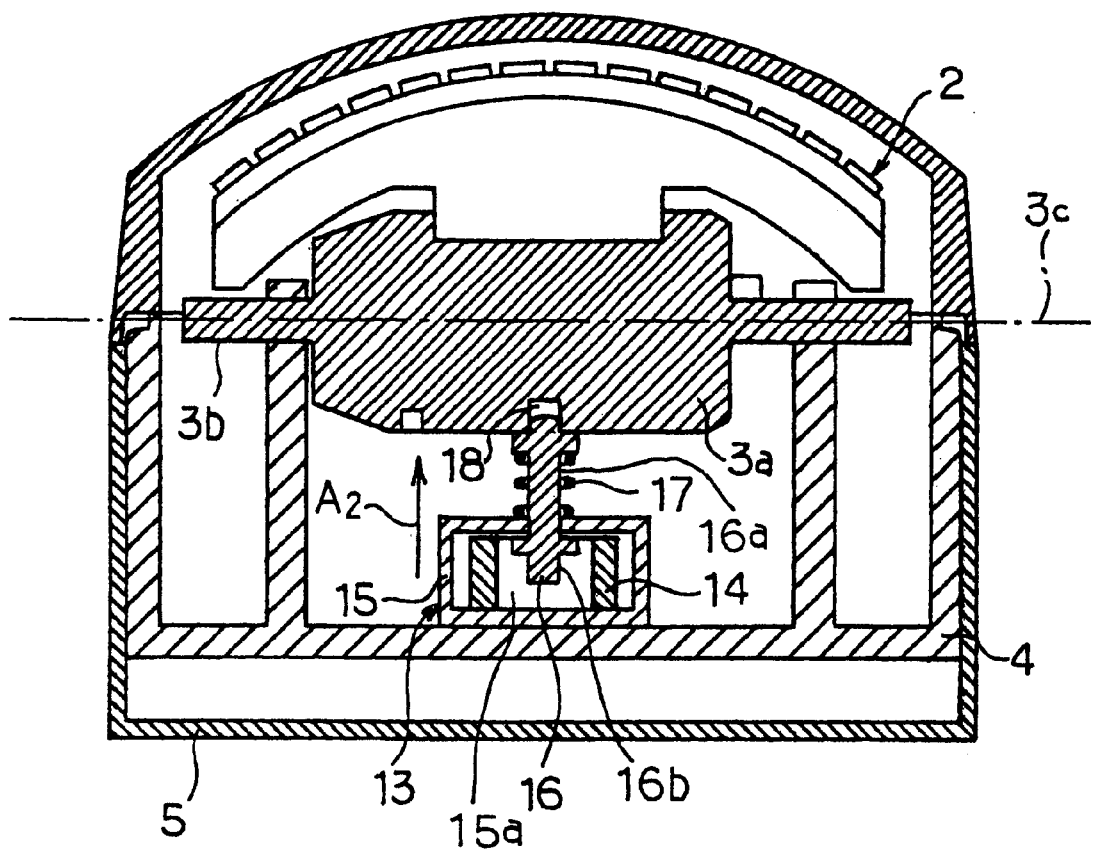
FIG. 4 is a cross-sectional view of the ultrasonic probe shown in FIG.1 when the brake mechanism is actuated.

As best shown in FIGS. 3 and 4, the brake mechanism 13 includes a magnetic frame 15, an electromagnet coil 14, an electromagnet shaft 16, and electromagnet shaft urging means 17.

The magnetic frame 15 is securely mounted on the frame structure 4 and formed with a chamber 15a therein. The electromagnet coil 14 is received in the chamber 15a of the magnetic frame 15 and partly secured to the magnetic frame 15. The electromagnet coil 14 is in the form of a cylindrical hollow shape.

The electromagnet shaft 16 is partly received in the chamber 15a of the magnetic frame 15 in axial alignment with the electromagnet coil 14 and supported by the magnetic frame 15. The electromagnet shaft 16 has a first longitudinal portion 16a projecting outwardly of the magnetic frame 15 and a second longitudinal portion 16b projecting inwardly of the electromagnet coil 14 and the magnetic frame 15. The electromagnet shaft 16 is axially movable with respect to the magnetic frame 15 and the electromagnet coil 14 to assume two operation states consisting of a first operation state under which the electromagnet shaft 16 is projected to an extremely projected position with respect to the electromagnet coil 14 and a second operation state under which the electromagnet shaft 16 is retracted to an extremely retracted position with respect to the electromagnet coil 14.

The electromagnet shaft urging means 17 is adapted to resiliently urge the electromagnet shaft 16 toward the first operation state under which the first longitudinal portion 16a of the electromagnet shaft 16 is partly brought into engagement with the cavity 18 of the electromagnet motor 3.

The first longitudinal portion 16a of the electromagnet shaft 16 is integrally formed with a first flange portion, and the second longitudinal portion 16b of the electromagnet shaft 16 is integrally formed with a second flange portion.

The electromagnet shaft urging means 17 is constituted by a helical coil spring 17 disposed to surround the first longitudinal portion 16a of the electromagnet shaft 16 and to have one end engaged with the first flange portion and the other end engaged with the electromagnet frame 15.

The description is now directed to the operation of the ultrasonic probe according to the present invention.

The brake mechanism 13 is firstly released to have the electromagnet coil 14 energized to cause a force of magnetic attraction between the magnetic frame 15 and the electromagnet shaft 16. Then, the force of magnetic attraction thus caused moves the electromagnet shaft 16 toward the direction designated by arrow A1 against the force of the electromagnet shaft urging means 17 as shown in FIG. 3. This means that the electromagnet shaft 16 axially moves with respect to the magnetic frame 15 and the electromagnet coil 14 to assume the second operation state, i.e., the electromagnet shaft 16 is retracted to the extremely retracted position with respect to the electromagnet coil 14 and brought out of engagement with the cavity 18 of the electromagnet motor 3, thereby making it possible for the rotor portion 3a to unrestrictedly rotate.

The brake mechanism 13, on the other hand, is actuated to have the electromagnet coil 14 de-energized to cease to generate the force of magnetic attraction between the magnetic frame 15 and the electromagnet shaft 16. The electromagnet shaft 16 is then resiliently urged toward the direction designated by arrow A2 by the electromagnet shaft urging means 17 as shown in FIG. 4. This means that the electromagnet shaft 16 axially moves with respect to the magnetic frame 15 and the electromagnet coil 14 to assume the first operation state, i.e., the electromagnet shaft 16 is projected to the extremely projected position with respect to the electromagnet coil 14, and the first longitudinal portion 16a of the electromagnet shaft 16 is partly brought into engagement with the cavity 18 of the electromagnet motor 3, thereby making it impossible for the rotor portion 3a to rotate.

The ultrasonic probe of the present embodiment can prevent the transducer 2 from rotating by actuating the brake mechanism 13 when the electromagnet motor 3 is stopped. The ultrasonic probe thus constructed makes it possible to protect the transducer 2 from a large shock caused by the electromagnet motor 3 especially when the ultrasonic probe is dropped.

In order to attain the objects of the present invention, the above first embodiment of the ultrasonic probe may be replaced by a second embodiment of the ultrasonic probe, which will be described hereinlater.

Figure 5:
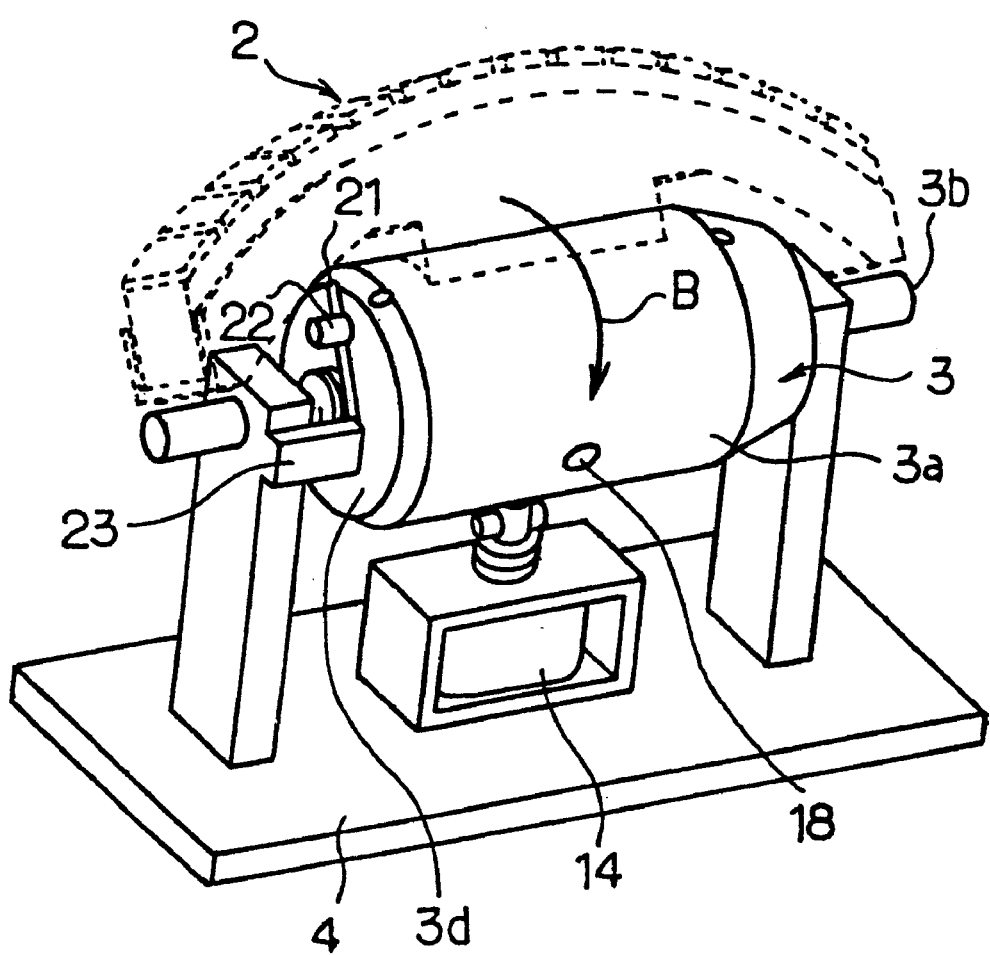
FIG. 5 is a fragmentary schematic view of a second embodiment of the ultrasonic probe according to the present invention.
Figure 6A:
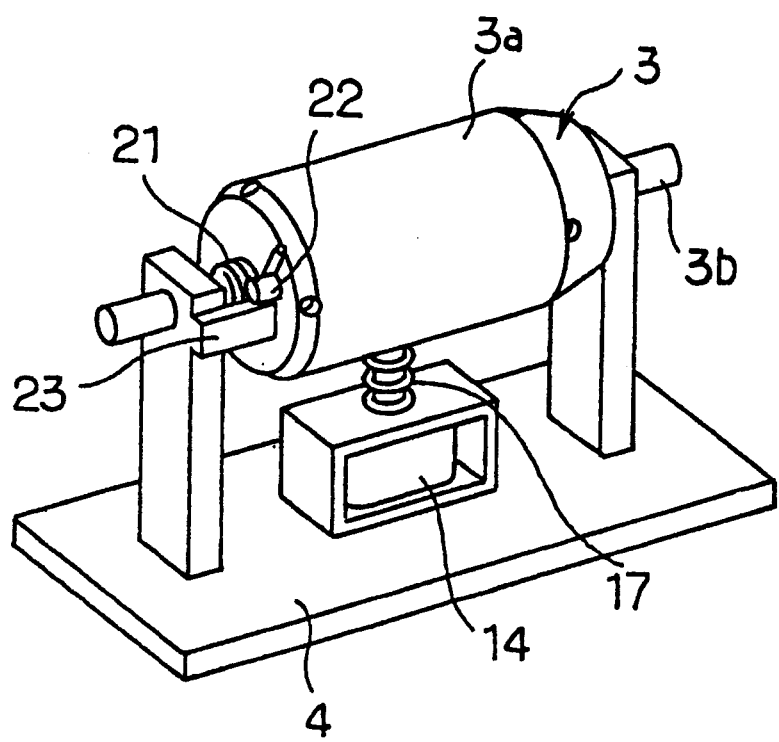
FIG. 6A is a fragmentary schematic view of the ultrasonic probe shown in FIG. 5 when a brake mechanism is actuated.
Figure 6B:
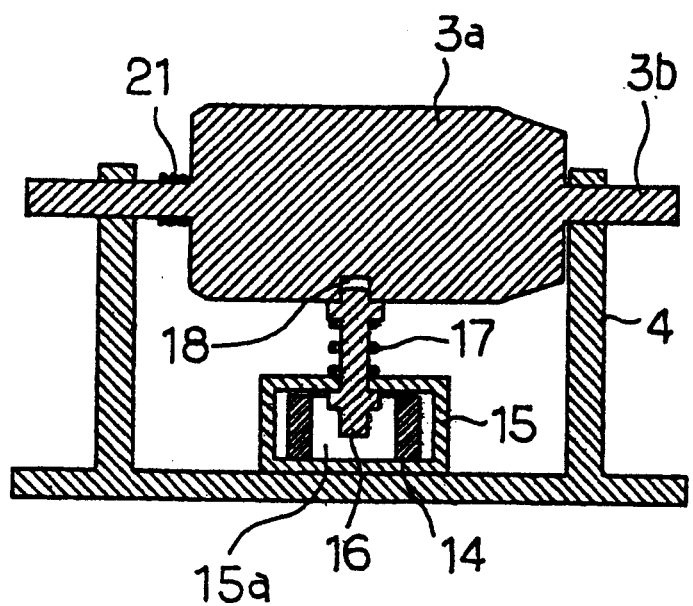
FIG. 6B is a fragmentary cross-sectional view of the ultrasonic probe shown in FIG. 5.

Referring to FIGS. 5, 6A, and 6B of the drawings, there is shown a second preferred embodiment of the ultrasonic probe embodying the present invention. The ultrasonic probe of the second embodiment is similar in construction to the first embodiment and thus includes elements the same in constitution and numeral reference as those of the ultrasonic probe of the first embodiment.

The electromagnet motor 3 is operative to assume a stop position under which the electromagnet motor 3 is stopped with respect to the frame structure 4 with the cavity 18 being in opposing relationship with the first longitudinal portion 16a of the electromagnet shaft 16.

The ultrasonic probe further comprises electromagnet motor urging means 21 for resiliently urging the electromagnet motor 3 toward the stop position of the electromagnet motor 3. This means that the electromagnet motor 3 is operative to assume a stop position under which the electromagnet motor 3 is stopped with respect to the frame structure 4 with the cavity 18 being in opposing relationship with the first longitudinal portion 16a of the electromagnet shaft 16

The ultrasonic probe further comprises electromagnet motor urging means 21 and electromagnet motor stopping means 22. The electromagnet motor urging means 21 is adapted to resiliently urge the electromagnet motor 3 in the rotation direction of the electromagnet motor 3 toward the stop position of the electromagnet motor 3. The electromagnet motor stopping means 22 is adapted to stop the electromagnet motor 3 from being rotated over the stop position. The electromagnet motor urging means 21 is constituted by a helical coil spring 21 having one end secured to the electromagnet motor 3 and the other end secured to the frame structure 4.

The electromagnet motor stopping means is constituted by a projected pin 22 and a stop member 23. The projected pin 22 is projected axially outwardly of the side surface 3d of the electromagnet motor 3. The projected pin 22 has a rotation path on which the projected pin 22 is rotatable together with the electromagnet motor 3. The stop member 23 is securely formed on the frame structure 4 to project to the rotation path of the projected pin 22 to ensure that the electromagnet motor 3 is resiliently urged by the helical coil spring 21 and stopped by the projected pin 22 and the stop member 23 under the stop state under which the cavity 18 is in opposing relationship with the first longitudinal portion 16a of the electromagnet shaft 16.

The description hereinlater is directed to the operation of the ultrasonic probe according to the present invention.

The electromagnet motor 3 is firstly actuated to have the rotor portion 3a driven to rotate against the force of the electromagnet motor urging means 21.

The electromagnet coil 14 is then energized to have the electromagnet coil 14 generate a force of magnetic attraction between the magnetic frame 15 and the electromagnet shaft 16. The force of magnet attraction thus generated moves the electromagnet shaft 16 against the force of the electromagnet shaft urging means 17 to assume the second operation state, i.e., the electromagnet shaft 16 is retracted to the extremely retracted position with respect to the electromagnet coil 14 and brought out of engagement with the cavity 18 of the electromagnet motor 3, thereby making it possible for the rotor portion 3a to rotate.

The electromagnet motor 3, on the other hand, is de-actuated to have the rotor portion 3a of the electromagnet motor 3 resiliently urged in the rotation direction designated by the arrow B toward the stop position by the electromagnet motor urging means 21 and stopped with respect to the frame structure 4 with the cavity 18 being in opposing relationship with the first longitudinal portion 16a of the electromagnet shaft 16 as shown in FIG. 5.

The electromagnet coil 14 is then de-energized to have the electromagnet coil 14 cease to generate the force of magnetic attraction between the magnetic frame 15 and the electromagnet shaft 16. The electromagnet shaft 16 is then resiliently urged by the electromagnet shaft urging means 17 toward the first operation state, i.e., the first longitudinal portion 16a of the electromagnet shaft 16 is partly brought into engagement with the cavity 18 of the electromagnet motor 3, thereby making it impossible for the rotor portion 3a to rotate as shown in FIGS. 6A and 6B.

In the ultrasonic probe of the second embodiment, the electromagnet motor 3 is resiliently urged toward the stop position by the electromagnet motor urging means 21 and stopped with respect to the frame structure 4 with the cavity 18 being opposing relationship with the first longitudinal portion 16a of the electromagnet shaft 16 regardless of the current rotation angle of the electromagnet motor 3 to ensure to prevent the electromagnet motor 3 from rotating.

The ultrasonic probe thus constructed makes it possible to protect the transducer 2 from a large shock caused by the electromagnet motor 3 especially when the ultrasonic probe is dropped.

In order to attain the objects of the present invention, the above second embodiment of the ultrasonic probe may be replaced by a third embodiment of the ultrasonic probe, which will be described hereinlater.

Figure 7:
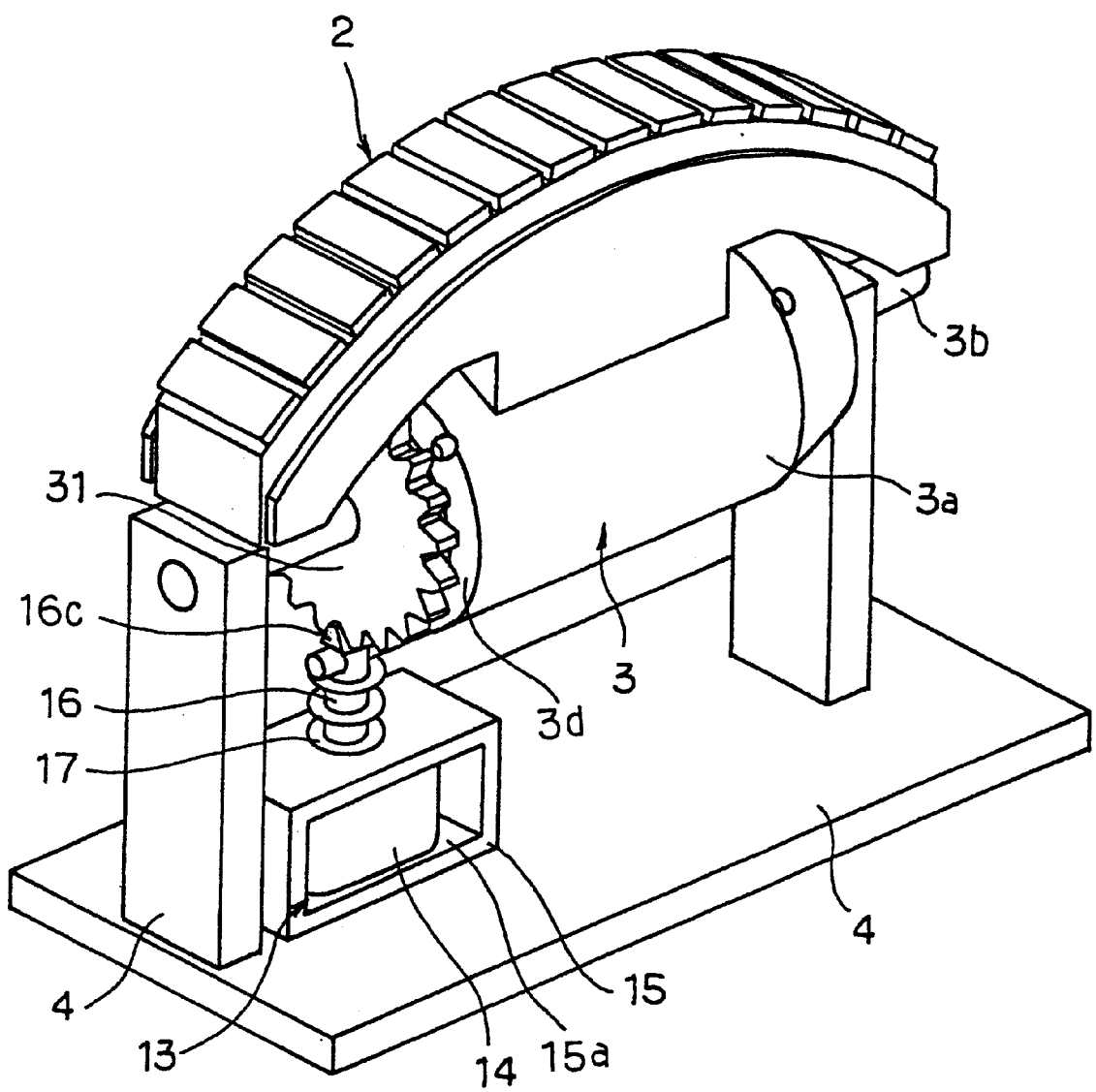
FIG. 7 is a fragmentary schematic view of a third embodiment of the ultrasonic probe according to the present invention.
Figure 8A:
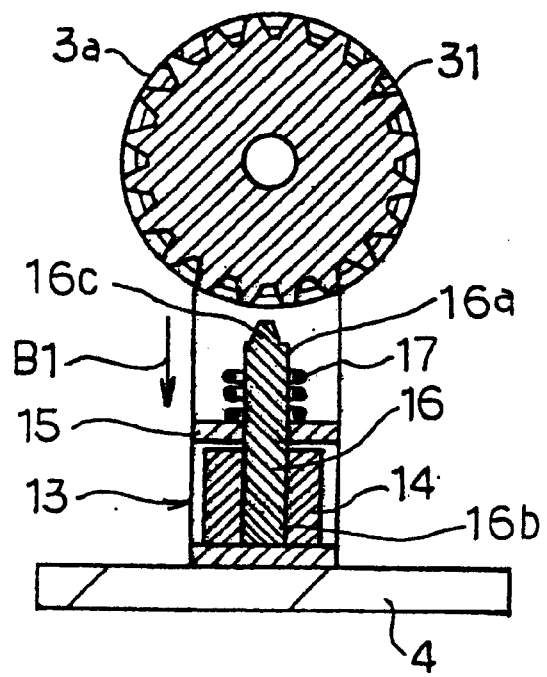
FIG. 8A is a fragmentary cross-sectional view of the ultrasonic probe shown in FIG. 7 when a brake mechanism is released.
Figure 8B:
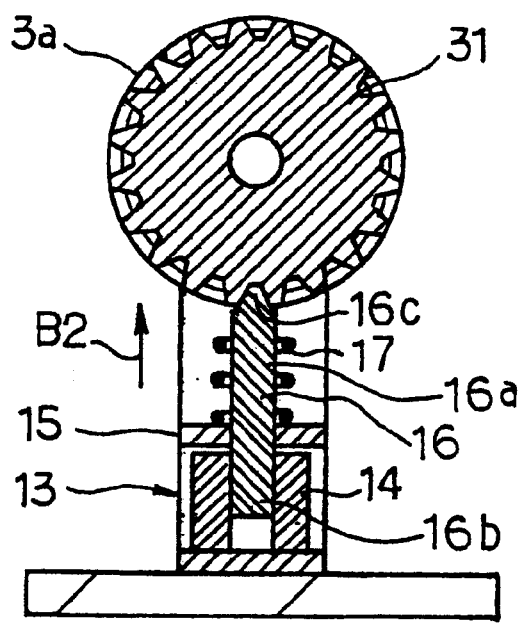
FIG. 8B is a fragmentary cross-sectional view of the ultrasonic probe shown in FIG. 7 when the brake mechanism is actuated.

Referring to FIGS. 7, 8A, and 8B of the drawings, there is shown a third preferred embodiment of the ultrasonic probe embodying the present invention. The ultrasonic probe of the third embodiment is similar in construction to the first embodiment and thus includes elements the same in constitution and numeral reference as those of the ultrasonic probe of the first embodiment.

In FIGS. 7, 8A, and 8B, the brake mechanism includes a gear member 31, a magnetic frame 15, an electromagnet coil 14, an electromagnet shaft 16, and electromagnet shaft urging means 17.

The gear member 31 has a center axis and is securely mounted on the side surface 3d of the electromagnet motor 3 with the center axis being aligned with the center axis 3c of the electromagnet motor 3. The gear member 31 has a plurality of teeth equally spaced apart from one another in the circumferential direction of the gear member 31, and a plurality of recesses each arranged and disposed between the adjacent two teeth, The magnetic frame 15 is securely mounted on the frame structure 4 and formed with a chamber 15a therein.

The electromagnet coil 14 is received in the chamber 15a of the magnetic frame 15 and partly secured to the magnetic frame 15. The electromagnet coil 14 is in the form of a cylindrical hollow shape.

The electromagnet shaft 16 is partly received in the chamber 15a of the magnetic frame 15 in axial alignment with the electromagnet coil 14 and supported by the magnetic frame 15 in opposing relationship with the gear member 31. The electromagnet shaft 16 has a first longitudinal portion 16a projecting outwardly of the magnetic frame 15 and a second longitudinal portion 16b projecting inwardly of the electromagnet coil 14 and the magnetic frame 15. The electromagnet shaft 16 is axially movable with respect to the magnetic frame 15 and the electromagnet coil 14 to assume two operation states consisting of a first operation state under which the electromagnet shaft 16 is projected to an extremely projected position with respect to the electromagnet coil 14 and a second operation state under which the electromagnet shaft 16 is retracted to an extremely retracted position with respect to the electromagnet coil 14. The first longitudinal portion 16a of the electromagnet shaft 16 has a leading end portion 16c in the form of a pawl shape.

The electromagnet shaft urging means 17 is adapted to resiliently urge the electromagnet shaft 16 toward the first operation state under which the leading portion 16c of the first longitudinal portion 16a of the electromagnet shaft 16 is partly brought into meshing engagement with one of the recesses of the gear member 31.

The description hereinlater is directed to the operation of the ultrasonic probe of the third embodiment.

The electromagnet motor 3 is actuated to have the electromagnet coil 14 energized to generate a force of magnetic attraction between the magnetic frame 15 and the electromagnet shaft 16. Then, the force of magnetic attraction thus generated moves the electromagnet shaft 16 in the direction designated by arrow B1 against the force of the electromagnet shaft urging means 17 as shown in FIG. 8A. This means that the electromagnet shaft 16 axially moves with respect to the magnetic frame 15 and the electromagnet coil 14 to assume the second operation state, i.e., the leading portion 16c of the first longitudinal portion 16a of the electromagnet shaft 16 is retracted to the extremely retracted position with respect to the electromagnet coil 14 and brought out of meshing engagement with one of the recesses of the gear member 31, thereby making it possible for the rotor portion 3a to unrestrictedly rotate.

The electromagnet coil 14, on the other hand, is de-energized to have the electromagnet coil 14 cease to generate the force of magnetic attraction between the magnetic flame 15 and the electromagnet shaft 16. The force of the electromagnet shaft urging means 17 then moves the leading portion 16c of the first longitudinal portion 16a of the electromagnet shaft 16 in the direction designated by arrow B2 toward the first operation state as shown in FIG. 8B. This means that the electromagnet shaft 16 axially moves to assume the first operation state under which the electromagnet shaft 16 is projected to the extremely projected position, i.e., the first longitudinal portion 16a of the electromagnet shaft 16 is partly brought into meshing engagement with one of the recesses of the gear member 31, thereby making it impossible for the rotor portion 3a to rotate as shown in FIG. 8B.

In the ultrasonic probe of the present embodiment, the leading portion 16c of the electromagnet shaft 16 is movable to be brought into meshing engagement with one of the recesses of the gear member 31 regardless of the current rotation angle of the electromagnet motor 3 to ensure to prevent the electromagnet motor 3 from rotating when the electromagnet motor 3 is stopped.

The ultrasonic probe thus constructed makes it possible to protect the transducer 2 from a large shock caused by the electromagnet motor 3 especially when the ultrasonic probe is dropped.

In order to attain the objects of the present invention, the above third embodiment of the ultrasonic probe may be replaced by a fourth embodiment of the ultrasonic probe, which will be described hereinlater.

Figure 9:
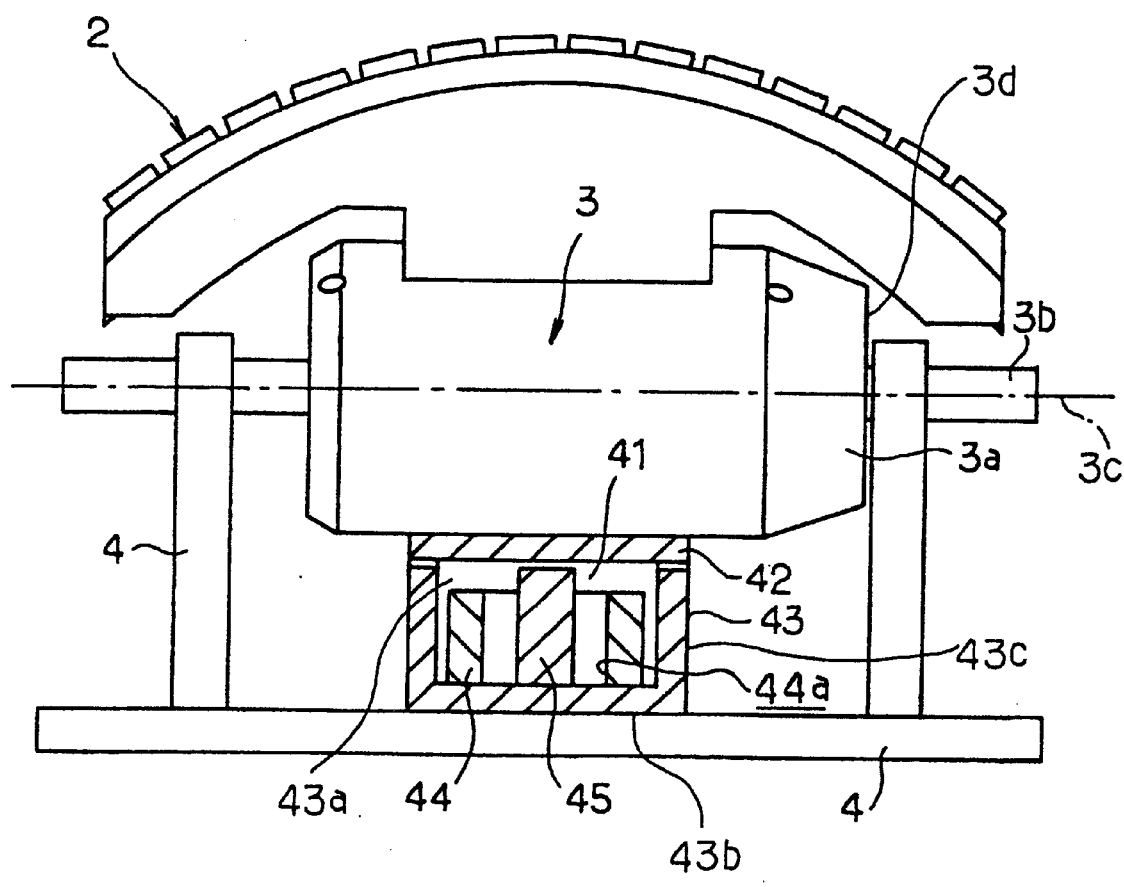
FIG. 9 is a fragmentary cross-sectional view of a fourth embodiment of the ultrasonic probe according to the present invention.
Figure 10:
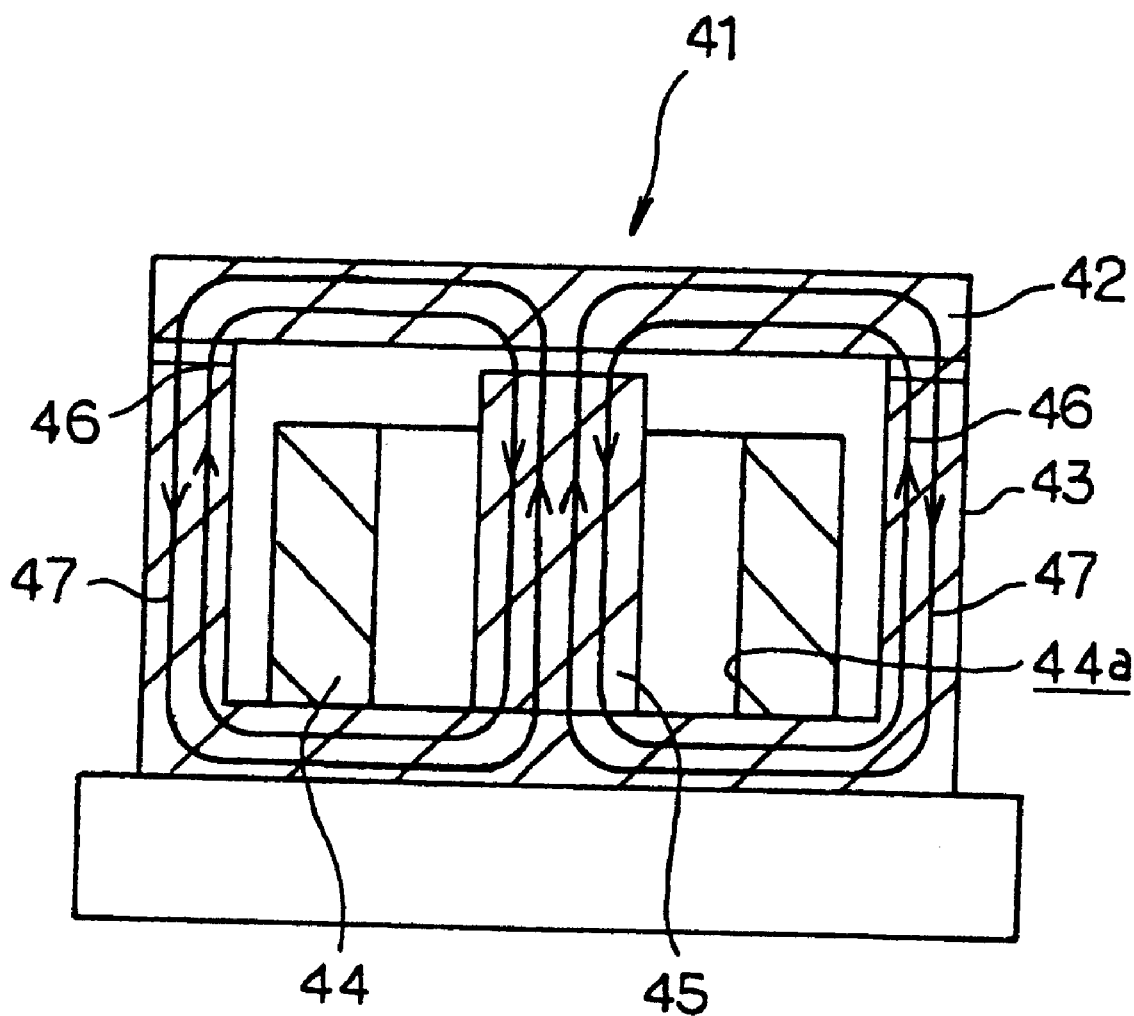
FIG. 10 is a cross-sectional view of a brake mechanism forming part of the ultrasonic probe shown in FIG. 9.

Referring to FIGS. 9 and 10 of the drawings, there is shown a fourth preferred embodiment of the ultrasonic probe embodying the present invention. The ultrasonic probe of the fourth embodiment is similar in construction to the first embodiment and thus includes elements the same in constitution and numeral reference as those of the ultrasonic probe of the first embodiment.

In FIGS. 9 and 10, the electromagnet motor 3 includes a rotor portion 3a having a center axis 3c and a pair of side surfaces 3d, and a pair of shaft portions 3b. Each of the shaft portions 3b has a center axis. The shaft portions 3b are respectively secured to the side surfaces 3d with the center axes being respectively in alignment with the center axis 3c of the rotor portion 3a and rotatably supported by the frame structure 4.

The brake mechanism 41 includes a first electromagnet member 42, a magnetic frame 43, an electromagnet coil 44, and a second electromagnet member 45 as shown in FIG. 10.

The first electromagnet member 42 is securely mounted on the peripheral wall of the rotor portion 3a of the electromagnet motor 3. The magnetic frame 43 is securely mounted on the frame structure 4 and formed with a chamber 43a therein.

The electromagnet coil 44 is received in the chamber 43a of the magnetic frame 43 and partly secured to the magnetic frame 43. The electromagnet coil 44 is in the form of a cylindrical hollow shape.

The second electromagnet member 45 is partly received in the chamber 43a of the magnetic frame 43 in axial alignment with the electromagnet coil 44 and supported by the magnetic frame 43 to be directed toward the first electromagnet member 42 to ensure that the first and second electromagnet members 42, 45 repel each other when the electromagnet coil 44 is energized.

The magnetic frame 43 includes a bottom wall portion 43b and a side wall portion 43c. The bottom wall portion 43b securely mounted on the frame structure 4, and the side wall portion 43c integrally formed with the bottom wall portion 43b. The bottom wall portion 43b and the side wall portion 43c of the magnetic frame 43 and the first electromagnet member 42 collectively define a chamber 43a to receive the electromagnet coil 44, the bottom wall portion 43b and the side wall portion 43c of the magnetic frame 43. The first electromagnet member 42, magnetic frame 43 and the second electromagnet member 45 are made of a magnetic substance.

The description hereinlater is directed to the operation of the ultrasonic probe of the fourth embodiment.

The electromagnet coil 44 is de-energized to have the second electromagnet member 45 create a magnetic flux 46 forming a magnetic circuit among the magnetic frame 43, the first electromagnet member 42, and the second electromagnet member 45 as shown in FIG. 10. The magnet flux 46 thus created causes a force of magnetic attraction between the second electromagnet member 45 and the first electromagnet member 42, which prevents the rotor portion 3a from rotating.

The electromagnet coil 44, on the other hand, is energized to create a magnetic flux 47, which counteracts the magnetic flux 46 as shown in FIG. 10. This means that the magnetic flux 47 thus created causes a force of repulsion to permit the second electromagnet member 45 and the first electromagnet member 42 to be repelled each other, thereby making it possible for the rotor portion 3a to unrestrictedly rotate.

In the ultrasonic probe of the fourth embodiment, the rotor portion 3a is stopped from rotating regardless of the current rotation angle of the electromagnet motor 3 to ensure to prevent the transducer 2 from rotating. The ultrasonic probe thus constructed makes it possible to protect the transducer 2 from a large shock caused by the electromagnet motor 3 especially when the ultrasonic probe is dropped. Furthermore, the brake mechanism 41 can be constructed without mechanical moving parts, thereby improving the performance and reliability of the ultrasonic probe.

The many features and advantages of the invention are apparent from the detailed specification, and thus it is intended by the appended claims to cover all such features and advantages of the invention which fall within the true spirit and scope thereof. Further, since numerous modifications and changes will readily occur to those skilled in the art, it is not desired to limit the invention to the exact construction and operation illustrated and described herein, and accordingly, all suitable modifications and equivalents may be construed as being encompassed within the scope of the invention.

What is claimed is:

1. An ultrasonic probe, comprising:
   a housing;
   a frame structure accommodated in said housing and held stationary with respect to said housing;
   an electromagnet motor rotatably supported by said frame structure in said housing;
   a transducer fixedly supported by said electromagnet motor in said housing to transduce an ultrasonic wave to and from an electric signal;
   a brake mechanism fixedly supported by said frame structure in said housing and operative to assume a braking state allowing said electromagnet motor to be braked and a brake-releasing state allowing said electromagnet motor to be released from being braked,
wherein said electromagnet motor is released from being braked by said brake mechanism when said electromagnet motor is driven to rotate while said electromagnet motor is braked by said brake mechanism when said electromagnet motor is stopped.

2. An ultrasonic probe as set forth in claim 1, in which said housing includes a bottom wall portion and a side wall portion integrally formed with said bottom wall portion to form a hollow chamber, and a window cover securely mounted on said side wall portion of said housing to form a closed chamber having said electromagnet motor received therein, said window cover being made of an ultrasonic wave transmission material to have said transducer transduce said ultrasonic wave to and from said electric signal.

3. An ultrasonic probe as set forth in claim 2, in which said window cover and said frame structure are combined to define a hermetically sealed chamber filling therein a coupling liquid to assist said transducer in transducing said ultrasonic wave to and from said electric signal.

4. An ultrasonic probe as set forth in claim 1, in which said transducer includes a main body having a top surface, and a plurality of piezoelectric elements arranged on said top surface of said main body in spaced relationship with one another along the center axis of said electromagnet motor.

5. An ultrasonic probe as set forth in claim 4, in which said piezoelectric elements are arranged on said main body of said transducer in spaced relationship with one another along the center axis of said electromagnet motor and each of said piezoelectric elements is in the form of a rectangular shape having a short side extending along the center axis of said electromagnet motor.

6. An ultrasonic probe as set forth in claim 3, in which said window cover has inner and outer surfaces arcuately formed and said main body of said transducer has an outer surface arcuately formed in parallel and spaced relationship with said inner surface of said window cover.

7. An ultrasonic probe as set forth in claim 1, in which said electromagnet motor includes a rotor portion having a center axis and a pair of side surfaces, and a pair of shaft portions each having a center axis, said shaft portions being respectively secured to said side surfaces with said center axes being respectively in alignment with said center axis of said rotor portions and rotatably supported by said frame structure.

8. An ultrasonic probe as set forth in claim 1, in which said frame structure includes a base plate portion, and a pair of stand portions spaced apart from each other along with the rotation axis of said electromagnet motor, and in which said electromagnet motor includes a rotor portion having a center axis and a pair of side surfaces, and a pair of shaft portions each having a center axis, said shaft portions being respectively secured to said side surfaces with said center axes being respectively in alignment with said center axis of said rotor portions and rotatably supported by said frame structure, said shaft portions being respectively rotatably supported by said stand portions of said frame structure.

9. An ultrasonic probe as set forth in claim 1, in which said electromagnet motor has a peripheral portion formed with a cavity, and
in which said brake mechanism includes,
a magnetic frame securely mounted on said frame structure and formed with a chamber therein,
an electromagnet coil received in said chamber of said magnetic frame and partly secured to said magnetic frame, said electromagnet coil being in the form of a cylindrical hollow shape,
an electromagnet shaft partly received in said chamber of said magnetic frame in axial alignment with said electromagnet coil and supported by said magnetic frame, said electromagnet shaft having a first longitudinal portion projecting outwardly of said magnetic frame and a second longitudinal portion projecting inwardly of said electromagnet coil and said magnetic frame, said electromagnet shaft being axially movable with respect to said magnetic frame and said electromagnet coil to assume two operation states consisting of a first operation state under which said electromagnet shaft is projected to an extremely projected position with respect to said electromagnet coil and a second operation state under which said electromagnet shaft is retracted to an extremely retracted position with respect to said electromagnet coil,
electromagnet shaft urging means for resiliently urging said electromagnet shaft toward said first operation state under which said first longitudinal portion of said electromagnet shaft is partly brought into engagement with said cavity of said electromagnet motor.

10. An ultrasonic probe as set forth in claim 9, in which said first longitudinal portion of said electromagnet shaft is integrally formed with a first flange portion, and said second longitudinal portion of said electromagnet shaft is integrally formed with a second flange portion, and in which said electromagnet shaft urging means is constituted by a helical coil spring disposed to surround said first longitudinal portion of said electromagnet shaft and to have one end engaged with said first flange portion and the other end engaged with said magnetic frame.

11. An ultrasonic probe as set forth in claim 9, in which said electromagnet motor is operative to assume a stop position under which said electromagnet motor is stopped with respect to said frame structure with said cavity being in opposing relationship with said first longitudinal portion of said electromagnet shaft, and which further comprises:
electromagnet motor urging means for resiliently urging said electromagnet motor toward said stop position of said electromagnet motor.

12. An ultrasonic probe as set forth in claim 9, in which said electromagnet motor is operative to assume a stop position under which said electromagnet motor is stopped with respect to said frame structure with said cavity being in opposing relationship with said first longitudinal portion of said electromagnet shaft, and which further comprises:
electromagnet motor urging means for resiliently urging said electromagnet motor in the rotation direction of said electromagnet motor toward said stop position of said electromagnet motor, and
electromagnet motor stopping means for stopping said electromagnet motor from being rotated over said stop position.

13. An ultrasonic probe as set forth in claim 12, in which said electromagnet motor urging means is constituted by a helical coil spring having one end secured to said electromagnet motor and the other end secured to said frame structure, and
said electromagnet motor stopping means is constituted by a projected pin projecting axially outwardly of said side surface of said electromagnet motor, said projected pin having a rotation path on which said projected pin is rotatable together with said electromagnet motor, and a stop member securely formed on said frame structure to project to said rotation path of said projected pin to ensure that said electromagnet motor is resiliently urged by said helical coil spring and stopped by said projected pin and said stop member under said stop state under which said cavity is in opposing relationship with said first longitudinal portion of said electromagnet shaft.

14. An ultrasonic probe as set forth in claim 1, in said brake mechanism includes,
- a gear member having a center axis and securely mounted on the side surface of said electromagnet motor with said center axis being aligned with said center axis of said electromagnet motor, said gear member having a plurality of teeth equally spaced apart from one another in the circumferential direction of said gear member, and a plurality of recesses each arranged and disposed between said adjacent two teeth,
- a magnetic frame securely mounted on said frame structure and formed with a chamber therein,
- an electromagnet coil received in said chamber of said magnetic frame and partly secured to said magnetic frame, said electromagnet coil being in the form of a cylindrical hollow shape,
- an electromagnet shaft partly received in said chamber of said magnetic frame in axial alignment with said electromagnet coil and supported by said magnetic frame and in opposing relationship with said gear member, said electromagnet shaft having a first longitudinal portion projecting outwardly of said magnetic frame and a second longitudinal portion projecting inwardly of said electromagnet coil and said magnetic frame, said electromagnet shaft being axially movable with respect to said magnetic frame and said electromagnet coil to assume two operation states consisting of a first operation state under which said electromagnet shaft is projected to an extremely projected position with respect to said electromagnet coil and a second operation state under which said electromagnet shaft is retracted to an extremely retracted position with respect to said electromagnet coil, said first longitudinal portion of said electromagnet shaft having a leading end portion (16c) in the form of a pawl shape,
- electromagnet shaft urging means for resiliently urging said electromagnet shaft toward said first operation state under which said leading portion (16c) of said first longitudinal portion of said electromagnet shaft is partly brought into meshing engagement with one of said recesses of said gear member.

15. An ultrasonic probe as set forth in claim 1, in which said electromagnet motor includes a rotor portion having a center axis and a pair of side surfaces, and a pair of shaft portions each having a center axis, said shaft portions being respectively secured to said side surfaces with said center axes being respectively in alignment with said center axis of said rotor portions and rotatably supported by said frame structure, and said brake mechanism includes,
- a first electromagnet member securely mounted on the peripheral wall of said rotor portion of said electromagnet motor,
- a magnetic frame securely mounted on said frame structure and formed with a chamber therein,
- an electromagnet coil received in said chamber of said magnetic frame and partly secured to said magnetic flame, said electromagnet coil being in the form of a cylindrical hollow shape,
- a second electromagnet member partly received in said chamber of said magnetic frame in axial alignment with said electromagnet coil and supported by said magnetic frame to be directed toward said first electromagnet member to ensure that said first and second electromagnet members repel each other when said electromagnet coil is energized.

16. An ultrasonic probe as set forth in claim 15, in which said magnetic flame includes,
- a bottom wall portion securely mounted on said frame structure, and a side wall portion integrally formed with said bottom wall portion, whereby said bottom wall portion and said side wall portion of said magnetic frame and said first electromagnet member collectively define a chamber to receive said electromagnet coil, said bottom wall portion and said side wall portion of said magnetic frame and said first electromagnet member is made of a magnetic substance.

\* \* \* \* \*

UNITED STATES PATENT AND TRADEMARK OFFICE
CERTIFICATE OF CORRECTION

PATENT NO.     : 6,423,008 B1
DATED          : July 23, 2002
INVENTOR(S)    : Eiichi Okawa and Takashi Suzuki It is certified that error appears in the above-identified patent and that said Letters Patent is hereby corrected as shown below:

Column 8,
Line 60, please delete "shaft 16" and insert -- shaft 16. --;

Column 10,
Line 21, please delete "teeth," and insert -- teeth. --;

Column 16,
Line 31, delete "flame" and insert -- frame --.

Signed and Sealed this

Eleventh Day of March, 2003

JAMES E. ROGAN
*Director of the United States Patent and Trademark Office*